May 7, 1974 R. G. LEIGHTY Plant Pat. 3,545
ROSE PLANT
Filed Jan. 2, 1973
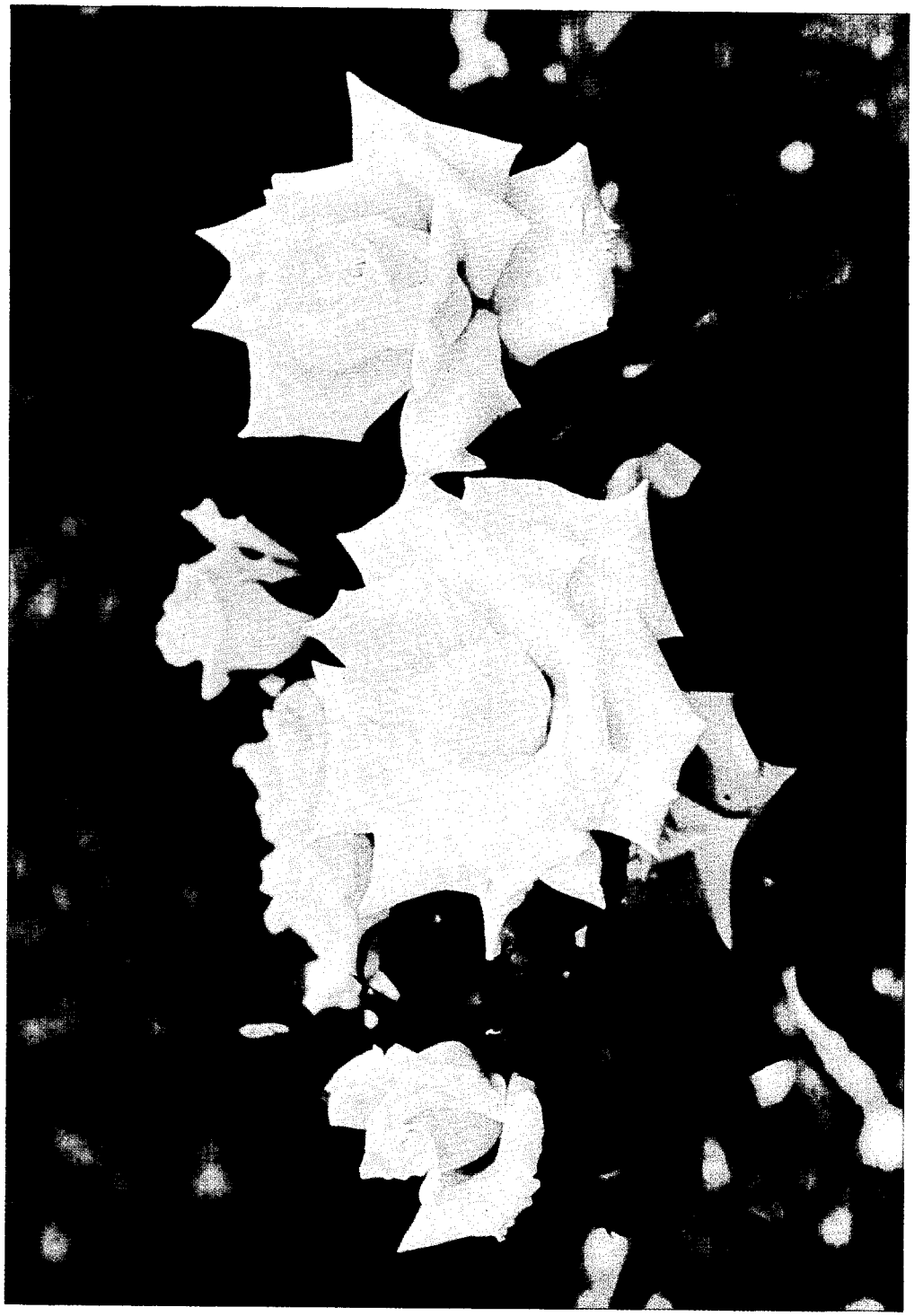

United States Patent Office

Plant Pat. 3,545

Patented May 7, 1974

3,545

ROSE PLANT

Ralph George Leighty, deceased, late of Gainesville, Fla., by Rosa Maria Arguelles Leighty, executrix, Gainesville, Fla., assignor to Robert W. Hyde, doing business as Hyde's House of Roses, Crystal River, Fla.

Filed Jan. 2, 1973, Ser. No. 320,665

Int. Cl. A01h 5/00

U.S. Cl. Plt.—23 1 Claim

The present invention relates to a new and distinct variety of rose plant of the floribunda class which was discovered by the late Ralph George Leighty as a cultivated sport of the rose variety known as "Gene Boerner" (Plant Pat. No. 2,885) in the cultivated rose garden at his home located in Gainesville, Florida.

At the time of the discovery aforesaid, Mr. Leighty was growing in his garden several plants of the variety "Gene Boerner," among many other rose varieties representative of most of the principal types of roses. During his care of his garden, before his death, his attention was attracted to one particular plant of the variety "Gene Boerner" which bore white flowers, contrary to the normal pink colored flowers that are characteristic of that variety. Close inspection of this particular plant showed that the white blooms were borne on only one cane of the plant which apparently had sported therefrom. After determining that the sport continued to bear white flowers, arrangements were made to graft budwood thereof onto Fortuniana root stock for further testing, as performed on his behalf at the University of Florida, at Gainesville. Continued observations and tests of the sport and its progeny showed that the white flower color remained stable, while all other characteristics of the sport were substantially identical to those of the variety "Gene Boerner," including its typical floribunda habit and vigorous, tall, well-branched, well-filled and well-shaped plant growth. These combined features set the new sport distinctly apart from all other white-flowered floribunda rose varieties, and accordingly represent a new and improved variety.

While there are several white or near white floribunda rose varieties, none have the habit of this new sport. Of those earlier varieties, only the variety known as "Saratoga" (Plant Pat. No. 2,299) has received general acceptance, but the form of its blooms is less appealing and the plants thereof are not as vigorous or as well-shaped. This is also true of the varieties known as "Iceberg" (unpatented) and "Ice White" (unpatented) which are not readily available and are not widely grown and are seldom catalogued.

The accompanying drawing shows typical specimens of the blooms and vegetative growth of the new variety in different stages of development, as depicted in color as nearly true as it is reasonably possible to make the same in a color illustration of this character.

Being substantially identical in all respects to the variety "Gene Boerner," except for a nearly pure white flower color during hot weather which becomes very slightly suffused with light pink or peachy pink tints during cold weather, but without streaking or strength gradation throughout all petals of the blooms as a whole, as distinguished from the bright pink blooms of "Gene Boerner," it is unnecessary to specifically describe the new sport in complete detail as more fully disclosed in Plant Pat. No. 2,885, issued May 6, 1969, to which reference may be readily had. However, for convenience, the following description of the new sport is given herein, with color terminolgy in accordance with Maerz and Paul Dictionary of Color, except where general color terms of ordinary dictionary significance are obvious:

Type: Hardy; tall (from about 6 to 8 feet); bush; outdoor; sport; for cut flowers and for garden decoration.

Class: Floribunda.

Parentage: Sport of "Gene Boerner."

Propagation: Holds its distinguishing characteristics through succeeding propagations by grafting.

*Flower*

Locality where grown and observed: Crystal River, Florida.

Flowers borne: 4 or 5 to stem; in irregular rounded clusters; on stems of normal strength and medium length.

Quantity of bloom: Abundant, outdoors.

Continuity: Continuous.

Fragrance: Slight.

Bud:

*Peduncle.*—Medium length; slender; stiff; entirely smooth; no thorns; few brown hairs. Color—Light green.

*Before calyx breaks.*—Size—Small. Form—Pointed; with a conspicuous neck; without foliaceous appendages on the surface of the bud; with slender, bristle-like foliaceous parts extending beyond the tip of the bud equal to ½ of its length. Color—Faint Yellow, Plate 9, line 1 C.

*As calyx breaks.*—Color—Faint Yellow, Plate 9, line 1 C.

*As first petal opens.*—Size—Small. Form—Pointed. Color—Outside—Faint Yellow, Plate 9, line 1 C. Inside—Faint Yellow, Plate 9, line 1 C.

*Opening.*—Opens up well.

Bloom:

*Size (when fully open).*—Medium; from about 2½ inches to 3½ inches.

*Petalage.*—Double (more petals, but stamens not hidden); from 22 to 25 petals; arranged regularly.

*Form.*—High-centered at first, but becoming open; petals at first being tightly rolled outward, but later becoming very loosely rolled outward at maturity.

Petals:

*Texture.*—Thin; soft.

*Appearance.*—Both inside and outside satiny.

*Shape.*—Outside—Round, with apex flat. Intermediate—Round; scalloped; with apex flat. Inside—Round.

This description of a newly opened flower was made from a rose grown outdoors during the month of June at Crystal River, Florida:

*Color.*—Outer petals: Outside surface—very faint yellow, but almost pure white; inside surface—very faint pink, but almost pure white. Intermediate petals: Outside surface—very faint pink; inside surface—same. Inner petals: Outside surface—very faint pink; inside surface—same.

This description was made from a rose that was open for three days outdoors during the month of June at Crystal River, Florida:

*Color.*—Outer petal: Outside surface—very faint; inside surface—same. Inner petal: Outside surface—very faint pink; inside surface—same.

*General color effect.*—Newly opened flower—almost pure white. 3-day open—no change; remains almost pure white.

*Behavior.*—Drop off cleanly; holds up well in hot or dry weather; slight suffusion of light pink or peachy pink during cold weather.

*Flower longevity.*—On bush in garden—4 days in June. Cut flowers grown outdoors and kept at living room temperature—3 days in June.

*Reproductive organs*

Stamens: Medium number; arranged regularly about pistils.
Filaments: Short.
*Color.*—White.
Pollen: Abundant.
*Color.*—Gold.
Pistils: Many.
Styles: Uneven; medium length; medium caliper; loosely separated.
Stigma:
*Color.*—Reddish purple.
Sepals: Falling soon; moderate length; recurved.

*Plant*

Foliage:
*Leaves.*—Compound of 3 leaflets; normal abundance; medium size; moderately thin; soft.
*Leaflets.*—Shape—Oval. Apex—Mucronate. Base—Round. Margin—Simply serrate.
*Color.*—Mature: Upper surface—normal green; under surface—moderately light green. Young: Upper surface—light green, with red edges; under surface—light green, with red edges.
*Rachis (the supporting stem of the compound leaf).*—Medium caliper. Upper side—Smooth. Under side—Moderately hairy.
*Stipules.*—Medium length; narrow; with points of medium length turning out at an angle of less than 45°.
Disease and insect resistance: Comparable to that of the variety "Gene Boerner," as determined by comparison with that variety and others grown under the same conditions at Crystal River and Gainesville, Florida.

Growth:
*Habit.*—Bushy; upright; well-branched; well-filled; well-shaped.
*Growth.*—Free; vigorous; tall.
*Canes.*—Medium caliper.
*Main stems.*—Color—Green and Bronze mottled. Thorns—Several; medium length; straight; with oval base. Prickles—None. Hairs—None.
*Branches.*—Color—Bright green. Thorns—Few; medium length; straight; with oval base. Prickles—None. Hairs—None.
*New shoots.*—Color—Bright green. Thorns—Very few; medium length; straight; with oval base. Prickles—None. Hairs—None.

What is claimed is:

1. A new and distinct variety of rose plant of the floribunda class, substantially as herein shown and described, characterized particularly as to novelty by being substantially identical in all respects, including the vigorous, tall, well-branched, well-filled and well-shaped habit of the rose variety known as "Gene Boerner" (Plant Pat. No. 2,885) except for its flower color, said flower color being essentially nearly pure white uniformly throughout during hot weather, but becoming very slightly suffused with light pink or peachy pink tints during cold weather, as distinguished from the normal bright pink flower color of "Gene Boerner" when grown under the same conditions.

No references cited.

ROBERT E. BAGWILL, Primary Examiner